United States Patent
McDonald et al.

(10) Patent No.: US 6,450,813 B1
(45) Date of Patent: Sep. 17, 2002

(54) REPAIR PORCELAIN PRODUCT, COMPOSITION AND METHOD

(75) Inventors: Albert F. McDonald, Wallingford, PA (US); Cha-Yang Chu, West Windsor, NJ (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/415,859

(22) Filed: Oct. 8, 1999

Related U.S. Application Data

(60) Provisional application No. 60/107,743, filed on Nov. 10, 1998.

(51) Int. Cl.⁷ ............................... A61K 6/06; C03C 8/02
(52) U.S. Cl. ..................... 433/212.1; 106/35; 501/59
(58) Field of Search .................... 433/212.1, 223; 106/35; 501/59

(56) References Cited

U.S. PATENT DOCUMENTS

| | | | |
|---|---|---|---|
| 4,189,325 A | 2/1980 | Barrett et al. | 106/35 |
| 4,198,244 A | 4/1980 | Hammer et al. | 260/17.3 |
| 4,437,192 A | 3/1984 | Fujiu et al. | 3/1.9 |
| 4,515,634 A | 5/1985 | Wu et al. | 106/35 |
| 4,652,312 A | 3/1987 | Grossman et al. | 106/35 |
| 4,789,649 A | 12/1988 | Abert et al. | 501/3 |
| 4,943,541 A | 7/1990 | Watanabe et al. | 501/10 |
| 5,066,619 A | 11/1991 | Kasuga et al. | 501/3 |
| 5,074,916 A | 12/1991 | Hench et al. | 106/35 |
| 5,120,340 A | 6/1992 | Ducheyne et al. | 65/18.3 |
| 5,125,971 A | 6/1992 | Nonami et al. | 106/35 |
| 5,246,889 A | 9/1993 | Kasuga et al. | 501/3 |
| 5,281,563 A * | 1/1994 | Komma et al. | 501/59 |
| 5,296,026 A | 3/1994 | Manroe et al. | 106/35 |
| 5,308,391 A | 5/1994 | Komma et al. | 106/35 |
| 5,346,866 A | 9/1994 | Komma et al. | 501/59 |
| 5,429,996 A | 7/1995 | Kaneko | 501/35 |
| 5,466,285 A | 11/1995 | Kamiya et al. | 106/35 |
| 5,507,981 A | 4/1996 | Petticrew | 264/16 |
| 5,552,350 A * | 9/1996 | Hornor | 501/64 |
| 5,591,030 A * | 1/1997 | Thiel et al. | 433/212.1 |
| 5,614,330 A * | 3/1997 | Panzera et al. | 428/697 |
| 5,622,551 A | 4/1997 | Erbe et al. | 106/35 |

(List continued on next page.)

FOREIGN PATENT DOCUMENTS

| | | |
|---|---|---|
| DE | 3911460 A1 | 10/1990 |
| DE | 4419015 A1 | 7/1995 |
| EP | 478937 A1 | 8/1991 |
| EP | 544145 A1 | 11/1992 |
| NL | 9200564 | 3/1992 |
| SU | 1549539 | 11/1987 |
| WO | WO 97/45377 | 12/1997 |

*Primary Examiner*—Ralph A. Lewis
(74) *Attorney, Agent, or Firm*—Dale R. Lovercheck; James B. Bieber

(57) ABSTRACT

The invention provides a dental porcelain product, comprising a core layer of core material and a repair layer of repair material. The core layer has a higher melting temperature than the repair layer. The core material comprising a portion of crystalline core material and a portion of glass core material. The repair material comprises a portion of crystalline repair material and a portion of glass repair material. The portion of crystalline core material is greater than the portion of the crystalline repair material. The core material and the repair material each are formed from powder materials and each comprising silicon dioxide, aluminum oxide, sodium oxide, potassium oxide, calcium oxide, cerium oxide and boron trioxide. Preferably, the core material comprises a component selected from the group consisting of barium oxide and titanium oxide. Preferably, the repair material comprises a component selected from a group consisting of lithium oxide, magnesium oxide and terbium oxide. Preferably, the core material comprises barium oxide and titanium oxide. Preferably, the repair material comprises lithium oxide, magnesium oxide and terbium oxide.

45 Claims, 2 Drawing Sheets

U.S. PATENT DOCUMENTS

| | | | | |
|---|---|---|---|---|
| 5,653,791 A | * | 8/1997 | Panzera et al. | 106/35 |
| 5,702,514 A | | 12/1997 | Petticrew | 106/35 |
| 5,713,994 A | * | 2/1998 | Kramer et al. | 106/35 |
| 5,922,628 A | * | 7/1999 | Barton et al. | 501/52 |
| 5,944,884 A | * | 8/1999 | Panzera et al. | 106/35 |
| 6,120,591 A | * | 9/2000 | Brodkin et al. | 106/35 |
| 6,187,701 B1 | * | 2/2001 | Sekino et al. | 501/67 |

* cited by examiner

REPAIR PORCELAIN PRODUCT, COMPOSITION AND METHOD

This application claims the benefit of US provisional patent application serial No. 60/107,743 filed Nov. 10, 1998.

This is a continuation-in-part of US provisional patent application serial No. 60/107,743 filed Nov. 10, 1998.

The invention relates to porcelain material. The invention provides a repair porcelain composition and method. The repair porcelain composition of the invention is a dental material for use with ceramic restorations in a metal free system, which can be used for fabrication of single unit dental restorations, such as crowns, veneers, inlays and onlays. Preferably the metal free system contains a pressed ceramic core (analogous to the metal copings in traditional porcelain-fused-to-metal dental crowns) and a low-fusing porcelain. The dental restoration is formed by building the porcelain over a pressed ceramic core and fusing the outer porcelain to the core material.

One of the major steps in preparation of metal free dental crowns is molding of a ceramic core. This step is fairly labor-intensive and time-consuming. Although it is unlikely to happen in the metal free system, sometimes the all-ceramic core copings or full-contours may contain internal imperfections, such as blisters, bubbles, chipped edges, etc. Copings with such imperfections normally need to be discarded, and a new coping needs to be made. Remaking a ceramic core is a costly and ineffective way to fix the problem.

Defective and/or damaged core copings of the prior art are not repaired, but are discarded. The invention effectively restores damaged core copings, by applying the repair porcelain. Use of repair porcelain of the invention allows laboratory technicians to repair the damaged core copings or full-contour crowns with no demarcation being detectable. Thus, an imperfect core coping can be restored to a perfectly esthetic crown, resulting in cost savings. The only known materials that have a similar function to the repair porcelain are the overglaze (D-OG) and the add-on (D-AO) porcelains in the Dicor glass-ceramic system.

The invention provides a dental porcelain product, comprising a core layer of core material and a repair layer of repair material. The core material has a core material melting temperature and the repair material has a repair material melting temperature. The core material melting temperature is higher than the repair material melting temperature. The core material comprising 58 to 64 percent by weight silicon dioxide, from 10 to 16 percent by weight aluminum oxide, from 4.5 to 8 percent by weight sodium oxide, from 9.5 to 12.0 percent by weight potassium oxide, and from 1 to 4 percent by weight boron trioxide. The repair material comprising 59 to 63 percent by weight $SiO_2$, 6 to 11 percent by weight $Al_2O_3$, 8 to 10 percent by weight $Na_2O$, from 7 to 10 percent by weight $K_2O$. The core material comprises a portion of crystalline core material and a portion of glass core material. The repair material comprises a portion of crystalline repair material and a portion of glass repair material. The portion of crystalline core material is greater than the portion of the crystalline repair material.

It is an object of the invention to provide a dental porcelain product, comprising a core layer of core material and a repair layer of repair material, the core layer being formed on a mold, the repair layer being formed on and integrally connected to a minor portion of the core layer, the core material comprising silicon dioxide and aluminum oxide and having a core material melting temperature and the repair material comprising silicon dioxide and aluminum oxide and having a repair material melting temperature, and the core material melting temperature effectively being higher than the repair material melting temperature.

It is an object of the invention to provide a method of making a dental porcelain product, comprising providing core material and a repair material, the core material effectively having a higher melting temperature than the repair material, the core material comprising a crystalline portion of core material and a glass portion of core material, the repair material comprising a crystalline portion of repair material and a glass portion of repair material, wherein the crystalline portion of core material is greater than the crystalline portion of the repair material, forming a core layer of the core material, the core layer having an outer surface, coating the repair material on a minor portion of the core layer outer surface.

It is an object of the invention to provide a dental porcelain product, comprising a core layer of core material and a repair layer of repair material, the core material having a core material melting temperature and the repair material having a repair material melting temperature, and the core material melting temperature is higher than the repair material melting temperature, wherein the core material comprises from 58 to 64 percent by weight silicon dioxide, from 10 to 16 percent by weight aluminum oxide, from 4.5 to 8 percent by weight sodium oxide, from 9.5 to 12.0 percent by weight potassium oxide, and from 1 to 4 percent by weight boron trioxide, and repair material comprises 59 to 63 percent by weight $SiO_2$, 6 to 11 percent by weight $Al_2O_3$, 8 to 10 percent by weight $Na_2O$, from 7 to 10 percent by weight $K_2O$, and core material comprises a portion of crystalline core material and a portion of glass core material, and the repair material comprises a portion of crystalline repair material and a portion of glass repair material, and the portion of crystalline core material is greater than the portion of the crystalline repair material.

Crystalline portion of core material as used herein refers to the crystalline portion by weight (for example in percent by weight) of dental ceramic crown core material.

Glass portion of core material as used herein refers to the glass portion by weight (for example in percent by weight) of dental ceramic crown core material.

Crystalline portion of repair material as used herein refers to the crystalline portion by weight (for example in percent by weight) of dental ceramic crown repair material.

Glass portion of repair material as used herein refers to the glass portion by weight (for example in percent by weight) of dental ceramic crown repair material.

Minor portion of a material as used herein refers to a portion by weight amounting to less than 50 percent by weight of the material.

Major portion of a material as used herein refers to a portion by weight amounting to more than 50 percent by weight of the material.

BRIEF SUMMARY OF THE INVENTION

The invention provides a dental porcelain product, comprising a core layer of core material and a repair layer of repair material, the core layer being formed on a mold, the repair layer being formed on and integrally connected to a minor portion of the core layer, the core material comprising silicon dioxide and aluminum oxide and having a core material melting temperature and the repair material comprising silicon dioxide and aluminum oxide and having a repair material melting temperature, and the core material melting temperature effectively being higher than the repair material melting temperature.

The invention provides a method of making a dental porcelain product, comprising providing core material and a repair material, the core material effectively having a higher melting temperature than the repair material, the core material comprising a crystalline portion of core material and a glass portion of core material, the repair material comprising a crystalline portion of repair material and a glass portion of repair material, wherein the crystalline portion of core material is greater than the crystalline portion of the repair material, forming a core layer of the core material, the core layer having an outer surface, coating the repair material on a minor portion of the core layer outer surface.

The invention provides a dental porcelain product, comprising a core layer of core material and a repair layer of repair material, the core material having a core material melting temperature and the repair material having a repair material melting temperature, and the core material melting temperature is higher than the repair material melting temperature, wherein the core material comprises from 58 to 64 percent by weight silicon dioxide, from 10 to 16 percent by weight aluminum oxide, from 4.5 to 8 percent by weight sodium oxide, from 9.5 to 12.0 percent by weight potassium oxide, and from 1 to 4 percent by weight boron trioxide, and repair material comprises 59 to 63 percent by weight $SiO_2$, 6 to 11 percent by weight $Al_2O_3$, 8 to 10 percent by weight $Na_2O$, from 7 to 10 percent by weight $K_2O$, and core material comprises a portion of crystalline core material and a portion of glass core material, and the repair material comprises a portion of crystalline repair material and a portion of glass repair material, and the portion of crystalline core material is greater than the portion of the crystalline repair material.

The invention provides a dental porcelain product, comprising a core layer of core material and a repair layer of repair material. The core layer has a higher melting temperature than the repair layer. The core material comprising a portion of crystalline core material and a portion of glass core material. The repair material comprises a portion of crystalline repair material and a portion of glass repair material. The portion of crystalline core material is greater than the portion of the crystalline repair material. The core material and the repair material each are formed from powder materials and each comprising silicon dioxide, aluminum oxide, sodium oxide, potassium oxide, calcium oxide, cerium oxide and boron trioxide. Preferably, the core material comprises a component selected from the group consisting of barium oxide and titanium oxide. Preferably, the repair material comprises a component selected from a group consisting of lithium oxide, magnesium oxide and terbium oxide. Preferably, the core material comprises barium oxide and titanium oxide. Preferably, the repair material comprises lithium oxide, magnesium oxide and terbium oxide.

DETAILED DESCRIPTION OF THE INVENTION

Figure 1:
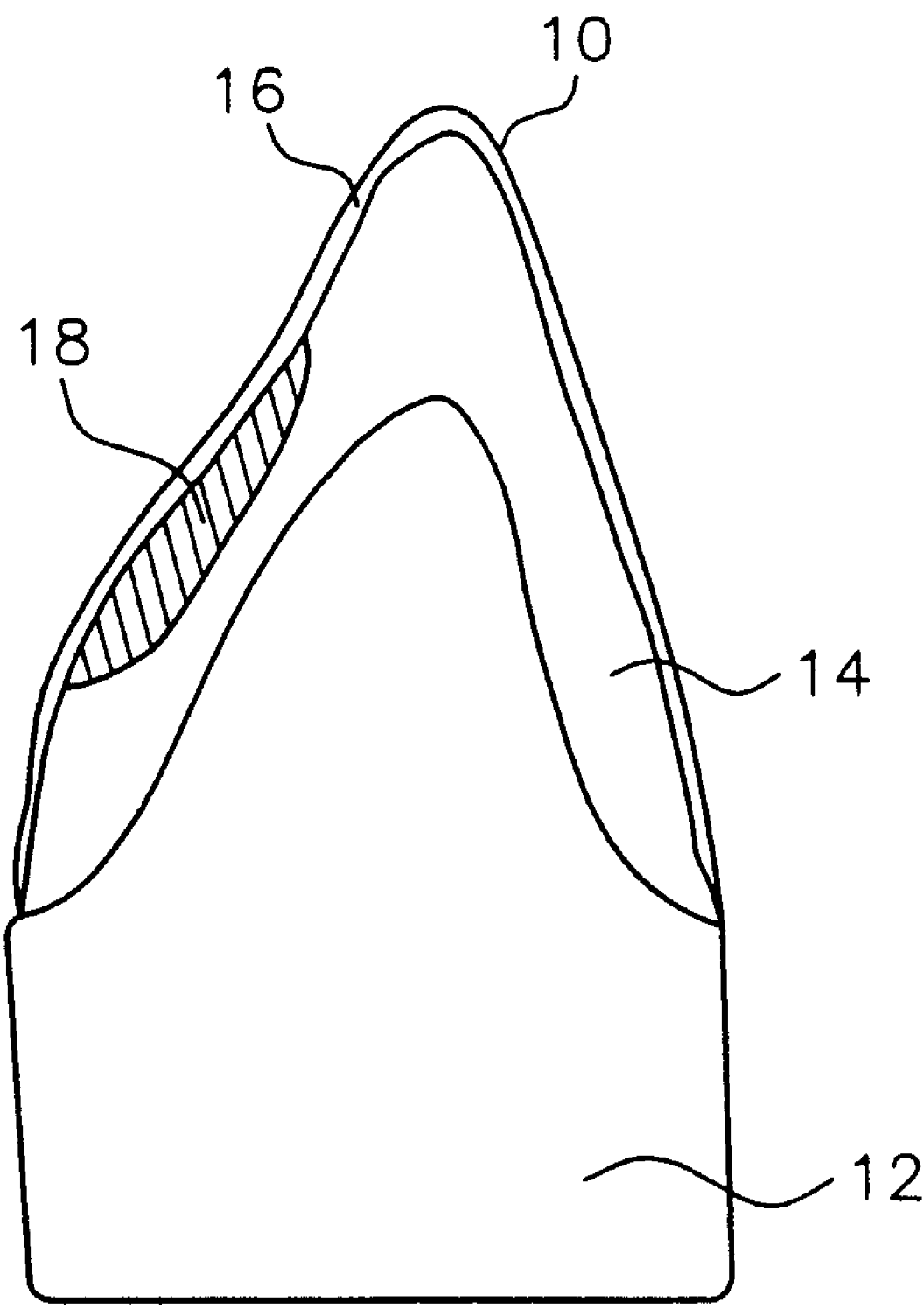
FIG. 1 is a cross-sectional schematic side view of a crown on a dye model being repaired in accordance with the invention.
Figure 2:
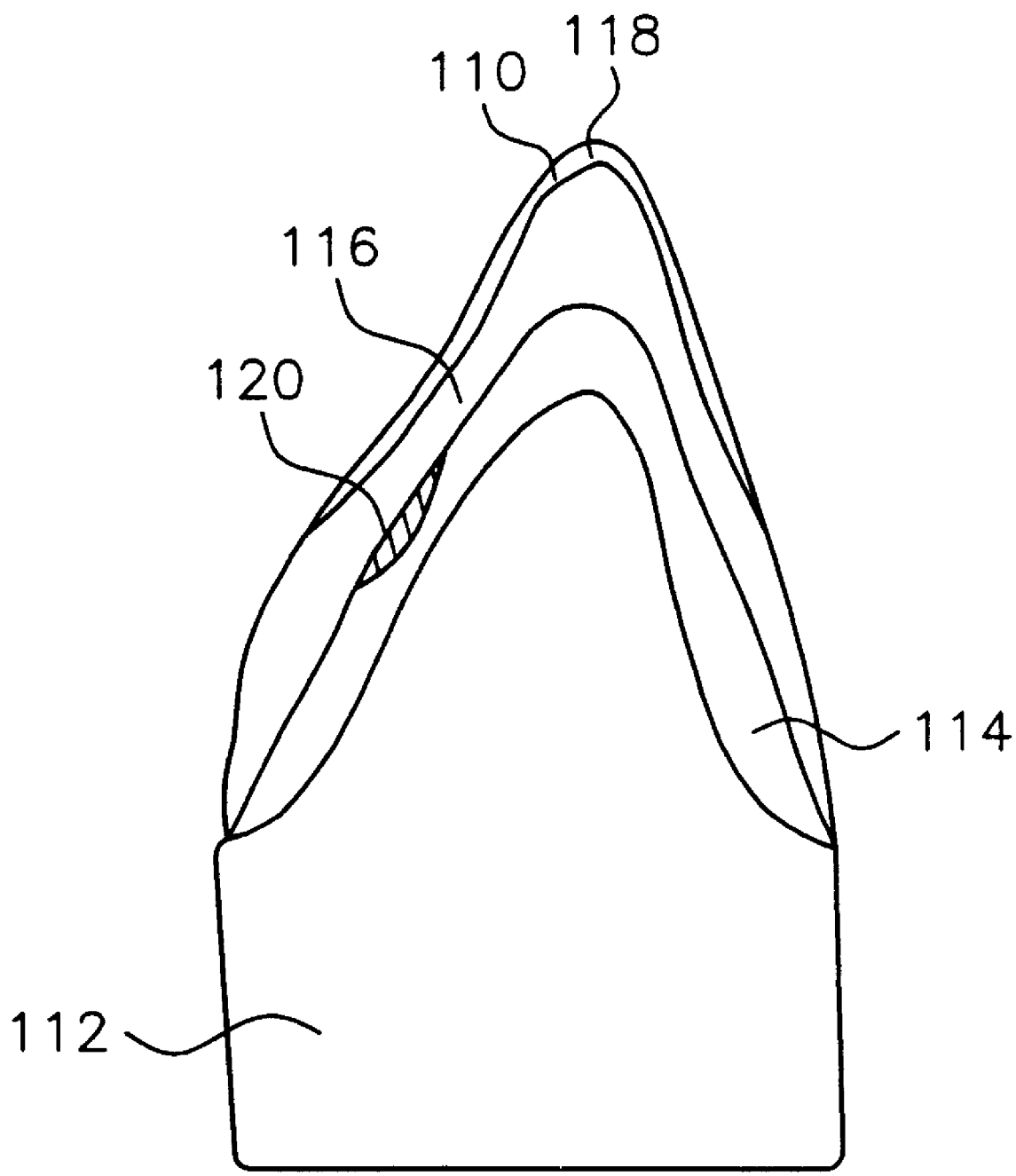
FIG. 2 is a cross-sectional schematic side view of a crown on a dye model being repaired in accordance with the invention.

The invention is now described with more particular reference to FIGS. 1 and 2. FIG. 1 shows a crown 10 on a die model 12. Crown 10 has core layer 14 and stain layer 16. Core layer 14 is repaired with integrally connected repair porcelain portion 18. Preferably, core 14 has an average thickness of from 0.9 to 2 mm or about 1.5 mm. Preferably, the repair porcelain portion 18 has an average thickness of from 0.05 to 1.4 mm or about 0.8 mm. Preferably, stain 16 has an average thickness of 0.3 mm.

With more particular reference to FIG. 2, is seen crown 110 on die mold 112. Crown 110 has a core layer 114, a dentin layer 116 and an enamel layer 118. Repair porcelain portion 120 is integrally connected to core layer 114 and dentin layer 116. Preferably, core layer 114 has an average of from 0.7 to 0.9 mm or about 0.8 mm. Preferably, dentin layer 116 has an average thickness of from 0.6 to 0.8 mm or about 0.7 mm. Preferably, repair porcelain portion 120 has an average thickness from about 0.1 mm to about 0.7 mm. Preferably, enamel layer 118 has an average thickness of from 0.3 to 0.5 or about 0.4 mm.

Repair porcelain compositions of the invention are used for repairing damaged core copings or full-contour crowns. The damages can be due to existence of blisters, bubbles, chipping, or other internal imperfections. Repair porcelain compositions of the invention may also be used to repair the marginal integrity of the restoration.

The repair porcelain is provided in powder form, in glass jars. To use, the repair porcelain powder is wetted with the Finesse carving liquid (manufactured by Ceramco Inc.) to form a paste for subsequent core repairing.

A preferred composition of the invention is shown in Table 1. Table 2 compares characteristics of, outer coating porcelain and Repair porcelains.

TABLE 1

Chemical composition of repair porcelain

| Composition | Formula | Example 1 repair porcelain |
|---|---|---|
| Silicon dioxide | $SiO_2$ | 62.38 |
| Aluminum oxide | $Al_2O_3$ | 10.50 |
| Sodium oxide | $Na_2O$ | 8.17 |
| Potassium oxide | $K_2O$ | 9.71 |
| Lithium oxide | $Li_2O$ | 1.89 |
| Calcium oxide | CaO | 1.80 |
| Magnesium oxide | MgO | 2.44 |
| Boron trioxide | $B_2O_3$ | 1.17 |
| Cerium oxide | $CeO_2$ | 0.12 |
| Terbium oxide | $Tb_2O_3$ | 1.82 |

TABLE 2

Other Characteristics of outer coating Porcelain, and repair porcelain (Example 1)

| Parameter | outer coating porcelain | Example 1 repair porcelain |
|---|---|---|
| Firing Temperature, °C. | 750–760 | 770 |
| CTE (ppm/° C.), @ 430° C./500° C. | 11.8/12.4 | 12.4/12.6 |
| Leucite Content, wt. % | 5.8 | ~16.0 |
| Contrast Ratio | 62.0 | 77.4 |

The repair porcelain of Example 1 allows repair of damaged ceramic cores and possesses the combination of properties (thermal expansion, firing temperature and color characteristics).

Some unique characteristics of the repair porcelain of the invention are:

The thermal expansion coefficient of the repair porcelain is close to both core material and outer coating porcelain (see Table 3).

The close match in thermal expansion coefficient assures the thermal compatibility can be obtained among repair porcelain, core, and outer coating porcelain. A mismatch in thermal expansion coefficient of these three components will result in cracking of the restoration or other drastic defects. Therefore, it is extremely important that the thermal expansion coefficient (from room temperature 23° C. to 430° C. ) of the Repair Porcelain is within the range between 11.8 ppm °C. (lowest specified CTE of outer coating porcelain) and 13.5ppm/°C. at 500° C. (highest specified CTE of FAC core).

TABLE 3

Thermal expansion coefficient of repair porcelain, core, and outer coating porcelain

| Material | temperature range | CTE (ppm /° C.) |
| --- | --- | --- |
| repair porcelain | 430° C./500° C. | 12.4/12.6 |
| core | 430° C./500° C. | 13.3/13.5 |
| outer coating porcelain | 430° C./500° C. | 11.8/12.4 |

The firing temperature of the repair porcelain of the invention is slightly higher than outer coating porcelain (see Table 4) and lower than the core material "slumping temperature".

The restoration is built in the following sequence: The core material is molded at 930° C. to form a coping or a full-contour crown. Next, the repair porcelain is applied and fired at 770° C., which is below the observed "slumping temperature" of the core material, to ensure the core shape retention. Outer coating porcelain is applied over the repaired core and fired at 760° -750° C. Since firing temperature of outer coating porcelain is lower than that of the repair porcelain (Example 1), no slumping of the repair porcelain occurs during outer coating porcelain firing. Repair porcelain (Example 1) slumping would result in bubbles and other visible flaws of restoration in the area of the repair porcelain application. This is highly undesirable and would defeat the purpose of the repair porcelain application

TABLE 4

Firing/"Slumping" Temperature of repair porcelain (Example 1), core, and outer coating porcelain

| Material | Firing/Slumping Temperature, ° C. |
| --- | --- |
| repair porcelain (Example 1) | 770 |
| core (slumping*) | 830–850 |
| Outer coating porcelain | 750–760 |

*FAC core slumping temperature is not an official term and is not scientifically defined. Here we refer to the temperature at which the initial loss of the core shape was observed by technicians.

The neutral color and the translucency of the repair porcelain (Example 1) allows it be placed in various areas of core material where the shades can be picked Up.

It is very important that the inherent color of the repair porcelain does not shine through the layer of Finesse build-up. Otherwise, the repaired areas will stand out from the rest of the crown and the restoration will lose its esthetic appearance.

An example of using the repair porcelain and its application technique is described below.

EXAMPLE 1

Portions of porcelain powder are mixed to form a blend which is 16 percent crystalline material and has the following repair porcelain composition:

| Composition | | Example 1 grams |
| --- | --- | --- |
| Silicon dioxide | $SiO_2$ | 62.38 |
| Aluminum oxide | $Al_2O_3$ | 10.50 |
| Sodium oxide | $Na_2O$ | 8.17 |
| Potassium oxide | $K_2O$ | 9.71 |
| Lithium oxide | $Li_2O$ | 1.89 |
| Calcium oxide | CaO | 1.80 |
| Magnesium oxide | MgO | 2.44 |
| Boron trioxide | $B_2O_3$ | 1.17 |
| Cerium oxide | $CeO_2$ | 0.12 |
| Terbium oxide | $Tb_2O_3$ | 1.82 |

EXAMPLE 2

Procedure for an Anterior Crown Preparation with Repair Porcelain

An impression of the patient's tooth is obtained by the doctor and forwarded to the dental laboratory for crown fabrication. A laboratory technician uses the patient's tooth impression to prepare a die stone model with removable dies. Then, the technician follows a standard procedure of model preparation for the wax-up, i.e. applies the die spacer over the model and allows it to harden completely. The laboratory chooses the most applicable crown fabrication technique, which may be Dentin/Enamel Layered Technique; Enamel Layered Technique; or Stain Technique. Depending on the technique chosen, a technician will wax-up a coping, cutback contour or full contour core. In this case the Dentin/Enamel Layered Technique is considered. This technique involves pressing of a ceramic coping, and building Finesse dentin and enamel over it to create a crown.

Phase One—Pressing of the Crown Core

During a coping wax-up, recreate all the necessary anatomic features in wax and completely seal the margins. Determine the weight of the wax pattern, choose the appropriate sprue base and sprue the wax pattern to the sprue base. Place the paper cylinder on the sprue base and the stabilizer ring on the other end of the cylinder. Prepare the investment liquid according to the manufacturer procedure. Carefully paint the waxed core with the investment to avoid defect formation during molding, and pour the remaining investment into the ring. Replace the stabilizer ring with the leveling ring to determine the proper height and angle of the investment for the pressing furnace. Prepare the investment ring for the wax burnout by letting the investment bench set. Place the rings into a burnout furnace preheated to 850° C. (1562° F. ). Heat soak the ring for 45–60 min, depending on the size of the ring. Simultaneously, preheat the alumina plunges in the same furnace. Select a core material ingot of the shade prescribed by the dentist (A0–D4). Once the ring has completed the burnout cycle, remove it from a burnout furnace and place it on a heat resistant surface with the sprue hole up. Carefully place the selected ingot into the sprue hole. Place the preheated plunger in the sprue hole on top of the ingot. Place the ring in the center of the firing platform of the Finesse Press pressing furnace. Start the furnace operation cycle. The ingot is pressed at 930° C., the pressing pressure is: 4.25 bars. After the pressing cycle has been completed, remove the ring from the furnace and cool rapidly.

Phase Two–Application of the repair porcelain.

Divest the cooled ring by removing all the investment material by sand blasting the pressed ceramic with fine glass beads at 20 psi. Then by inspecting the divested coping product for flaws, both internal and external flaws are found which developed during waxing, casting and finishing of a crown. Thus, for each coping which appears to have a bubble, a blister or a chipped edge, a portion of the repair porcelain formed in Example 1 is applied to conceal and/or otherwise correct these imperfections and/or errors. Application of the repair porcelain at this point of the crown fabrication leads to a successful completion of a flaw restoration.

The repair porcelain is applied by a technician to the restoration as follows:

1. Relieve the flawed area of the restoration with a fine stone, diamond burr or a coarse rubber wheel. If repairing an internal bubble, grind surface down to the base of the bubble. Taper the ground area away from the base of the repair gradually to the surface of the crown. This will ensure a more even blend of the repair porcelain and the core material of the crown. This is important to achieve the proper esthetic results.
2. Sandblast the repair area with 25 micron aluminum oxide powder, applying the pressure of 20–25 psi. Clean the restoration with steam or use Ultra-Sonic Distilled water bath.
3. Apply repair porcelain formed by following the procedure of Example 1 to the prepared surface and overbuild allowing for shrinkage during firing. Condense dry and brush to feather joint area.
4. Fire the restoration at the following schedule:

Repair Porcelain Firing Schedule

| Dry Time | Pre-heat Time | Vacuum Hold | High Temp. Hold | Cool Time | Idel Temp. | High Temp. | Heat Rate (Per Minute) |
| --- | --- | --- | --- | --- | --- | --- | --- |
| 5 min | 5 min | 0 min | 0.5 min | 0 min | 450° C. (842° F.) | 770° C./ (418° F.) | 35° C. (63° F.) |

5. After cooling, finish with a fine stone or diamond burr or a coarse rubber wheel. Surface with a fine diamond and a sandblast with 25 micron aluminum oxide at low pressure. Steam clean or place in Ultrasonic cleaner with distilled water before Finesse porcelain application.

Repair porcelain of Example 1 has a lower firing temperature than the ceramic core material (porcelain) it is applied to for repair. Repair porcelain of Example 1 has a higher firing temperature than the outer coating porcelain. Repair porcelain of Example 1 can be used with ceramic core material and outer coating porcelains under multiple firing conditions without overfiring, discoloring or loss of form.

Phase Three—Porcelain Application

Apply and fire the opaceous dentin, dentin and/or enamel porcelain to complete the restorations. The final crown shade is checked using a composite die material. Apply the stain and/or glaze over the restoration and fire it. The restoration is completed.

The complete restoration must be etched prior to placement into the patient's mouth. This step is typically performed in the laboratory. The crown is steam cleaned, then the Finesse etchant is applied to the bonding surfaces of the restoration for 1–2 minutes. After the etchant is removed the crown is placed into the neutralizer solution for about 20 seconds, then cleaned with steam or distilled water and placed on the die model to prevent the contamination of the etched surface.

Placement of the Prepared Crown in to the Patient's Mouth.

The crown is bonded to the prepared tooth by the doctor with a light-curing or dual curing new generation cement and adhesive system (e.g. EnForce® with Fluoride Resin Cement and Prime & Bond® 2.1 Dental adhesive system, DENTSPLY, Caulk, Milford, Del. ).

In the patient's mouth the provisional restoration is removed from the prepared tooth and the area is cleaned and dried. The fit of the restoration is verified, and the prepared tooth is isolated with a rubber dam and retainer. The Prime & Bond® 2.1 dental adhesive is applied to the prepared tooth and light-cured. The internal aspects of the restoration are treated with a silane coupling agent and EnForce® with Fluoride resin cement is applied to the bonding surfaces of the restoration. Then the restoration is seated, the cement excess is removed and the entire restoration is light-cured from all the surfaces. As a last step, the crown is adjusted and finished with fine diamonds and polishers.

In accordance with a preferred embodiment of the invention is provided a repair composition including about 62.38 percent by weight Silicon dioxide ($SiO_2$), about 10.50 percent by weight Aluminum oxide ($Al_2O_3$), about 8.17 percent by weight Sodium oxide ($Na_2O$), about 9.71 percent by weight Potassium oxide ($K_2O$), about 1.89 percent by weight Lithium oxide ($Li_2O$), about 1.80 percent by weight Calcium oxide (CaO), about 2.44 percent by weight Magnesium oxide (MgO), about 1.17 percent by weight Boron trioxide ($B_2O_3$), about 0.12 percent by weight Cerium oxide ($CeO_2$); and about 1.82 percent by weight Terbium oxide ($Tb_2O_3$). Preferably this repair composition is applied as a powder blend to core material formed from a composition including about 63.5 percent by weight Silicon dioxide ($SiO_2$), about 14.5 percent by weight Aluminum oxide ($Al_2O_3$), about 7.3 percent by weight Sodium oxide ($Na_2O$), about 9.8 percent by weight Potassium oxide ($K_2O$), about 1.6 percent by weight Calcium oxide (CaO), about 0.8 percent by weight Barium oxide, about 0.6 percent by weight Cerium oxide ($CeO_2$), about 0.2 percent by weight Titanium oxide; and about 1.7 percent by weight Boron trioxide. Preferably, an outer coating is supported by the repair composition. The outer coating including about 60.82 percent by weight Silicon dioxide ($SiO_2$), about 8.53 percent by weight Aluminum oxide ($Al_2O_3$), about 9.24 percent by weight Sodium oxide ($Na_2O$), about 9.51 percent by weight Potassium oxide ($K_2O$), about 2.27 percent by weight Lithium oxide ($Li_2O$), about 2.02 percent by weight Calcium oxide (CaO), about 3.22 percent by weight Magnesium oxide (MgO), about 1.75 percent by weight Boron trioxide ($B_2O_3$), about 0.15 percent by weight Cerium oxide ($CeO_2$); and about 2.49 percent by weight Terbium oxide ($Tb_2O_3$).

In accordance with a preferred embodiment of the invention is provided a dental porcelain product, comprising a core layer of core material and a repair layer of repair material. The core layer has a higher melting temperature than the repair layer. The core material and the repair material each are formed from powder blend material comprising silicon dioxide, aluminum oxide, sodium oxide, potassium oxide, calcium oxide, cerium oxide and boron trioxide. The core material comprises a component selected from the group consisting of barium oxide and titanium oxide. The repair material comprises a component selected from a group consisting of lithium oxide, magnesium oxide and terbium oxide. Preferably, the core material comprises barium oxide and titanium oxide. Preferably, the repair material comprises lithium oxide, magnesium oxide and terbium oxide. Preferably, the product is a dental crown. Preferably, the product is formed by pressing at temperatures above the melting point of the core material, and then firing. The core layer melts in the pressing step. The repair layer melts in the firing step. The core layer effectively does not melt in the firing step.

Preferably repair porcelain composition of the invention includes from 58 to 64 percent by weight $SiO_2$, from 5 to 12 percent by weight $Al_2O_3$, from 7 to 11 percent by weight $Na_2O$, from 6 to 11 percent by weight $K_2O$, from 0 to 4 percent by weight $Li_2O$, from 0 to 4 percent by weight CaO, from 0 to 5 percent by weight MgO, from 0 to 3 percent by weight $B_2O_3$, from 0 to 1 percent by weight $CeO_2$ and from 0 to 5 percent by weight $Tb_2O_3$. Most preferably, repair porcelain composition of the invention includes from 59 to 63 percent by weight $SiO_2$, from 6 to 11 percent by weight $Al_2O_3$, from 8 to 10 percent by weight $Na_2O$, from 7 to 10 percent by weight $K_2O$, from 0 to 3 percent by weight $Li_2O$, from 0 to 3 percent by weight CaO, from 1 to 4 percent by weight MgO, from 0 to 2 percent by weight $B_2O_3$, from 0 to 0.5 percent by weight $CeO_2$ and from 1 to 4 percent by weight $Tb_2O_3$.

Preferably, core material used in accordance with the invention includes from 57 to 65 percent by weight $SiO_2$, from 9 to 17 percent by weight $Al_2O_3$, from 4 to 9 percent by weight $Na_2O$, from 8.5 to 13 percent by weight $K_2O$, from 0 to 5 percent by weight CaO, from 0 to 4 percent by weight BaO, from 0 to 2 percent by weight $CeO_2$ and from 0 to 3 percent by weight $Tb_2O_3$, from 1 to 5 percent by weight $B_2O_3$. Most preferably, core material used in accordance with invention includes from 58 to 64 percent by weight $SiO_2$, from 10 to 17 percent by weight $Al_2O_3$, from 4.5 to 8 percent by weight $Na_2O$, from 9.5 to 12 percent by weight $K_2O$, from 1 to 4 percent by weight CaO, from 0 to 3 percent by weight BaO, from 0 to 1 percent by weight $CeO_2$, from 0 to 1.5 percent by weight $TiO_2$ and from 1 to 4 percent by weight $B_2O_3$.

In accordance with a preferred embodiment of the invention is provided a dental porcelain product, comprising a core layer of core material and a repair layer of repair material, the core layer being formed on a mold, the repair layer being formed on and integrally connected to a minor portion of the core layer, the core material comprising silicon dioxide and aluminum oxide and having a core material melting temperature and the repair material comprising silicon dioxide and aluminum oxide and having a repair material melting temperature, and the core material melting temperature effectively being higher than the repair material melting temperature. Preferably the core material comprises a crystalline portion of core material and a glass portion of core material, the repair material comprises a crystalline portion of repair material and a glass portion of repair material, and the crystalline portion of core material is greater than the crystalline portion of the repair material. Preferably the crystalline portion of core material is more than 1 percent greater than the crystalline portion of the repair material. Preferably the crystalline portion of core material is more than 3 percent greater than the crystalline portion of the repair material. Preferably the crystalline portion of core material is more than 5 percent greater than the crystalline portion of the repair material. Preferably the dental porcelain product further comprises a dentin layer of dentin material, the dentin layer being formed on and integrally connected to a major portion of the core layer, the dentin material comprising silicon dioxide and aluminum oxide and having a dentin material melting temperature, the repair material melting temperature being higher than the dentin material melting temperature. Preferably the dentin material comprises a crystalline portion of dentin material and a glass portion of dentin material, and the crystalline portion of repair material is effectively greater than the crystalline portion of the dentin material. Preferably the crystalline portion of repair material is more than 3 percent greater than the crystalline portion of the dentin material. Preferably the crystalline portion of core material is more than 5 percent greater than the crystalline portion of the repair material. Preferably the dental porcelain product further comprises a enamel layer of enamel material, the enamel layer being formed on and integrally connected to a major portion of the dentin layer, the enamel material comprising silicon dioxide and aluminum oxide and having a enamel material melting temperature, the dentin material melting temperature being higher than the enamel material melting temperature. Preferably the enamel material comprises a crystalline portion of enamel material and a glass portion of enamel material, and the crystalline portion of the dentin material is effectively greater than the crystalline portion of the enamel material. Preferably the crystalline portion of dentin material is more than 3 percent greater than the crystalline portion of the enamel material. More preferably the crystalline portion of dentin material is more than 5 percent greater than the crystalline portion of the enamel material.

In accordance with a preferred embodiment of the invention is provided a method of making a dental porcelain product, comprising providing core material and a repair material, the core material effectively having a higher melting temperature than the repair material, the core material comprising a crystalline portion of core material and a glass portion of core material, the repair material comprising a crystalline portion of repair material and a glass portion of repair material. Preferably the crystalline portion of core material is greater than the crystalline portion of the repair material, forming a core layer of the core material, the core layer having an outer surface, coating the repair material on a minor portion of the core layer outer surface. Preferably the core material and the repair material are each formed from powder material comprising silicon dioxide, aluminum oxide, sodium oxide, potassium oxide, calcium oxide, cerium oxide and boron trioxide, the core material comprising a titanium oxide the repair material comprising a component selected from a group consisting of lithium oxide, magnesium oxide and terbium oxide. Preferably the core layer is formed on a mold, the repair layer is integrally connected to the minor portion of the core layer. Preferably the core material has a melting temperature the repair material has a melting temperature, and the core material melting temperature effectively is higher than the repair material melting temperature. Preferably the core material comprises a crystalline portion of core material and a glass portion of core material, the repair material comprises a crystalline portion of repair material and a glass portion of repair material, and the crystalline portion of core material is greater than the crystalline portion of the repair material. Preferably the crystalline portion of core material is more than 1 percent greater than the crystalline portion of the repair material.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making a dental porcelain product, comprising:
   providing a core material and a repair material, said core material having a core material melting temperature, said repair material having a repair material melting temperature, and said core material melting temperature being higher than said repair material melting temperature,
   said core material comprising 58 to 64 percent by weight silicon dioxide, from 10 to 16 percent by weight aluminum oxide, from 4.5 to 8 percent by weight sodium oxide, from 9.5 to 12.0 percent by weight potassium oxide,
   said repair material comprising 59 to 63 percent by weight $SiO_2$, 6 to 11 percent by weight $Al_2O_3$, 8 to 10 percent by weight $Na_2O$, from 7 to 10 percent by weight $K_2O$,
   said core material comprising a crystalline portion of core material and a portion of glass core material,
   said repair material comprising a crystalline portion of repair material and a portion of glass repair material,
   said crystalline portion of core material being greater than said crystalline portion of said repair material,
   molding said core material into a core layer having an outer surface,
      firing said core layer at a first temperature whereby a fired core is formed having at least one internal imperfection under a minor portion of said core layer outer surface,
      removing said minor portion of said outer surface from over said internal imperfection to form a depression,
         coating said repair material on said depression to form a repaired core, said repair material having an average thickness from about 0.1 mm to about 0.7 mm,
         firing said repaired core at a second temperature to form a dental porcelain product,
         said second temperature being sufficiently lower than said first temperature so that said core layer effectively does not melt during said firing of said repaired core at a second temperature.

2. The method of claim 1 wherein said core material melting temperature is at least 50° C. higher than said repair material melting temperature.

3. The method of claim 1 wherein said core material melting temperature is at least 80° C. higher than said repair material melting temperature.

4. The method of claim 1 wherein said product is a dental crown.

5. The method of claim 1 wherein said portion of crystalline core material is at least 1 percent more than said portion of crystalline repair material.

6. The method of claim 1 wherein said portion of crystalline core material is at least 2 percent more than said portion of crystalline repair material.

7. The method of claim 1 wherein said product is formed by pressing said core material at temperatures above the melting point of the core material and then firing.

8. The method of claim 1 further comprising pressing said core material and wherein said core material melts during said pressing and repair material melts during said firing, and said core layer effectively does not melt during said firing.

9. The method of claim 7 wherein said pressing is at about 930° C.

10. The method of claim 1 wherein said core material further comprises from 1 to 4 percent by weight MgO, from 1 to 4 percent by weight boron trioxide and from 1 to 4 percent by weight $Tb_2O_3$.

11. The method of claim 1 wherein said repair material further comprises from 1 to 4 percent by weight MgO and from 1 to 4 percent by weight $Tb_2O_3$.

12. The method of claim 1 wherein said repair layer has an average thickness of from about 0.1 mm to about 0.7 mm.

13. The method of claim 1 wherein said repair layer has an average thickness of from 0.05 to 1.4 mm.

14. The method of claim 1 wherein said repair material has a coefficient of thermal expansion of from 11.8 ppm/° C. to 13.5 ppm/° C. between 23° C. and 430° C.

15. The method of claim 1 wherein said repair material has a coefficient of thermal expansion of from 12.4 ppm/° C. to 12.6 ppm/° C. between 430° C. and 500° C.

16. A method of making a dental porcelain crown product, comprising:
   providing a core material, and a repair material, said core material having a higher melting temperature than said repair material,
   said core material comprising a portion of crystalline core material and a portion of glass core material,
   said repair material comprising a portion of crystalline repair material and a portion of glass repair material,
   said portion of crystalline core material being greater than said portion of said crystalline repair material,
   said repair material having an average thickness from about 0.1 mm to about 0.7 mm,
   molding said core material into a core layer having an outer surface,
   firing said core layer at a first temperature to form a depression in a minor portion of said core layer outer surface,
   coating said repair material on said depression to form a repaired core,
   firing said repaired core at a second temperature to form a dental porcelain product,
   said second temperature being sufficiently lower than said first temperature so that said core layer effectively does not melt during said firing of said repaired core at a second temperature,
   said depression and said repair material having a thickness from about 2 percent to about 95% of the thickness of said core layer immediately adjacent to said repair.

17. The method of claim 16 wherein said depression and said repair material have a thickness of from about 0.1 mm to about 0.7 mm.

18. The method of claim 16 wherein said depression and said repair material have a thickness of from 0.05 to 14 mm.

19. The method of claim 16 wherein said repair matyerial has a coefficient of thermal expansion of from 11.8 ppm/° C. to 13.5 ppm/° C. between 23° C. and 430° C.

20. The method of claim 16 wherein said repair material has a coefficient of thermal expansion of from 12.4 ppm/° C. to 12.6ppm/° C. between 430° C. and 500° C.

21. A method of making a dental porcelain product, comprising:
   providing a core material and a repair material, said core material having a higher melting temperature than said repair material, said core material comprising a portion of crystalline core material and a portion of glass core material, said repair material comprising a portion of crystalline repair material and a portion of glass repair material, said portion of crystalline core material being greater than said portion of said crystalline repair material said core material and said repair material each being formed from powder material comprising silicon dioxide, aluminum oxide, sodium oxide, potassium oxide, calcium oxide, cerium oxide and boron trioxide, said core material comprising a titanium oxide, said repair material comprising a component selected from a group consisting of lithium oxide, magnesium oxide and terbium oxide, molding said core material into a core layer having an outer surface, firing said core layer at a first temperature to form a depression in a minor portion of said core layer outer surface, coating said repair material on said depression to form a repaired core, said repair material having an average thickness from about 0.1 mm to about 0.7 mm, firing said repaired core at a second temperature to form a dental porcelain product, said second temperature being sufficiently lower than said first temperature so that said core layer effectively does not melt during said firing of said repaired core at a second temperature.

22. The method of claim 21 wherein said repair layer has an average thickness of from about 0.1 mm to about 0.7 mm.

23. The method of claim 21 wherein said repair layer has an average thickness of from 0.05 to 1.4 mm.

24. The method of claim 21 wherein said repair material has a coefficient of thermal expansion of from 11.8 ppm/° C. to 13.5 ppm/° C. between 23° C. and 430° C.

25. The method of claim 21 wherein said repair material has a coefficient of thermal expansion of from 12.4 ppm/° C. to 12.6 ppm/° C. between 430° C. and 500° C.

26. A method of making a dental porcelain product, comprising providing a core material and a repair material, said core material comprising silicon dioxide and aluminum oxide and having a core material melting temperature and said repair material comprising silicon dioxide and aluminum oxide and having a repair material melting temperature, and said core material melting temperature effectively being higher than said repair material melting temperature, molding said core material into a core layer having an outer surface, firing said core layer at a first temperature to form a depression in a minor portion of said core layer outer surface, coating said repair material on said depression to form a repaired core, said repair material having an average thickness from about 01 mm to about 0.7 mm, firing said repaired core at a second temperature to form a dental porcelain product, said second temperature being sufficiently lower than said first temperature so that said core layer effectively does not melt during said firing of said repaired core at a second temperature.

27. The method of claim 26 wherein said core material comprises a crystalline portion of core material and a glass portion of core material, said repair material comprises a crystalline portion of repair material and a glass portion of repair material, and said crystalline portion of core material is greater than said crystalline portion of said repair material.

28. The method of claim 27 wherein said crystalline portion of core material is more than 1 percent greater than said crystalline portion of said repair material.

29. The method of claim 27 wherein said crystalline portion of core material is more than 3 percent greater than said crystalline portion of said repair material.

30. The method of claim 27 wherein said crystalline portion of core material is more than 5 percent greater than said crystalline portion of said repair material.

31. The method of claim 26 wherein said dental porcelain product further comprises a dentin layer of dentin material, said dentin layer being formed on and integrally connected to a major portion of said core layer, said dentin material comprising silicon dioxide and aluminum oxide and having a dentin material melting temperature, said repair material melting temperature being higher than said dentin material melting temperature.

32. The method of claim 31 wherein said dentin material comprises a crystalline portion of dentin material and a glass portion of dentin material, and said crystalline portion of repair material is effectively greater than said crystalline portion of said dentin material.

33. The method of claim 32 wherein said crystalline portion of repair material is more than 3 percent greater than said crystalline portion of said dentin material.

34. The method of claim 32 wherein said crystalline portion of core material is more than 5 percent greater than said crystalline portion of said repair material.

35. The method of claim 26 wherein said dental porcelain product further comprises a enamel layer of enamel material and a dentin layer of dentin material, said enamel layer being formed on and integrally connected to a major portion of said dentin layer, said enamel material comprising silicon dioxide and aluminum oxide and having an enamel material melting temperature, said dentin material melting temperature being higher than said enamel material melting temperature.

36. The method of claim 35 wherein said enamel material comprises a crystalline portion of enamel material and a glass portion of enamel material, and said crystalline portion of said dentin material is effectively greater than said crystalline portion of said enamel material.

37. The method of claim 36 wherein said crystalline portion of dentin material is more than 3 percent greater than said crystalline portion of said enamel material.

38. The method of claim 36 wherein said crystalline portion of dentin material is more than 5 percent greater than said crystalline portion of said enamel material.

39. A method of making a dental porcelain product, comprising:

providing core material and a repair material, said core material effectively having a higher melting temperature than said repair material, said core material comprising a crystalline portion of core material and a glass portion of core material, said repair material comprising a crystalline portion of repair material and a glass portion of repair material, said crystalline portion of core material being greater than said crystalline portion of said repair material, forming a core layer of said core material, said core layer having an outer surface, firing said core layer at a first temperature whereby a fired core is formed having at least one internal imperfection under a minor portion of said core layer outer surface, removing said minor portion of said outer surface from over said internal imperfection to form an imperfect base, coating said repair material on said imperfect base to form repair layer of a repaired core, said repair material of said repair layer having an average thickness from about 0.1 mm to about 0.7 mm and firing said repaired core at a second temperature to form a dental porcelain product, said second temperature being sufficiently lower than said first temperature so that said core layer effectively does not melt during said firing of said repaired core at a second temperature.

40. The method of claim 39 wherein said core material and said repair material are each formed from powder material comprising silicon dioxide, aluminum oxide, sodium oxide, potassium oxide, calcium oxide, cerium oxide and boron trioxide, said core material comprising a titanium oxide said repair material comprising a component selected from a group consisting of lithium oxide, magnesium oxide and terbium oxide.

41. The method of claim 39 wherein said core layer is formed on a mold, said repair layer is integrally connected to said minor portion of said core layer.

42. The method of claim 39 wherein said core material has a melting temperature said repair material has a melting temperature, and said core material melting temperature effectively is higher than said repair material melting temperature.

43. The product of claim 39 wherein said core material comprises a crystalline portion of core material and a glass portion of core material, said repair material comprises a crystalline portion of repair material and a glass portion of repair material, and said crystalline portion of core material is greater than said crystalline portion of said repair material.

44. The method of claim 43 wherein said crystalline portion of core material is more than 1 percent greater than said crystalline portion of said repair material.

45. The method of claim 29 wherein said internal imperfection is a blister or bubble.

\* \* \* \* \*